US00PP35775P2

(12) United States Plant Patent
Olesen

(10) Patent No.: US PP35,775 P2
(45) Date of Patent: Apr. 30, 2024

(54) MINIATURE ROSE PLANT NAMED 'POULPAH112'

(50) Latin Name: *Rosa hybrida*
Varietal Denomination: Poulpah112

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/445,476

(22) Filed: Sep. 8, 2023

(30) Foreign Application Priority Data

Sep. 30, 2022 (QZ) ..... PBR 2022/2160

(51) Int. Cl.
*A01H 5/02* (2018.01)
*A01H 6/74* (2018.01)

(52) U.S. Cl.
USPC ..... Plt./118

(58) Field of Classification Search
USPC ..... Plt./101, 116, 118
See application file for complete search history.

*Primary Examiner* — Susan McCormick Ewoldt

(57) ABSTRACT

A new garden rose plant of the Miniature class which has abundant, yellow flowers and attractive foliage. This new and distinct variety has shown to be uniform and stable in the resulting generations from asexual propagation.

1 Drawing Sheet

Botanical designation: *Rosa hybrida.*

Variety denomination: 'Poulpah112 '.

This application claims priority to Plant Breeder's Rights Application Number 2022/2160, which was filed at the Community Plant Variety Rights Office in the European Union on Sep. 26, 2022, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulpah112', originated as a single seedling from the stated cross.

The new variety may be distinguished from its male pollen parent and female seed parent primarily by the following characteristics. The male pollen parent plant has orange flowers while the new variety has yellow flowers. The female seed parent plant grows to a height of 40 cm while the new variety grows to a height of 55 cm.

The objective of the hybridization of this rose variety was to create a new and distinct variety with unique qualities, such as:

1. Uniform and abundant yellow flowers with long lasting quality;
2. Vigorous, but compact growth when propagated on its own roots;
3. Exceptional disease resistance.

This combination of qualities is not present in previously available commercial cultivars of this type, known to the inventor, and distinguish 'Poulpah112' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulpah112' was selected in the spring of 2015 by the inventor as a single plant from the progeny of the aforementioned hybridization.

Asexual reproduction of 'Poulpah112' by rooted cuttings was first done by Mogens N. Olesen in the nursery in Fredensborg, Denmark in July, 2015. This initial and other subsequent asexual propagations conducted in controlled environments have demonstrated that the characteristics of 'Poulpah112' are true to type and are transmitted from one generation to the next.

DESCRIPTION OF THE DRAWING

The accompanying color illustration shows, as true as is reasonably possible to obtain in color photographs of this type, the typical characteristics of the buds, flowers, leaves, and stems, of 'Poulpah112'. Specifically illustrated in the drawing are open flowers viewed from above and the side, flower petals and sepals detached revealing reproductive flower parts, flower pedicel and receptacle, mature and juvenile foliage, and bare stem exhibiting prickles. Plants shown are 5 months old.

DETAILED DESCRIPTION OF THE VARIETY

The following is a description of 'Poulpah112', as observed in its growth in an indoor glasshouse in Odense Denmark. Observed plants are 5 months of age, and were grown on their own roots in 19 cm pots. Color references are made using The Royal Horticultural Society (London, England) Colour Chart, 2001, except where common terms of color are used.

For a comparison, several physical characteristics of the rose variety 'Poulpah088', U.S. Plant Pat. No. 29,717 are compared to the claimed plant. While 'Poulpah112' has 38 flower petals, 'Poulpah088' has 70 flower petals. The claimed plant has a flower diameter of 70 mm while 'Poulpah088' has a flower diameter of 90 mm. Open flowers of 'Poulpah112' are generally Yellow Group 6A in color while 'Poulpah088' has a general tonality of Yellow Group 10A.

FLOWER AND FLOWER BUD

Blooming habit: Continuous.

Flower bud:

*Size.*—Upon opening, 20 mm in length from base of receptacle to end of bud. Bud diameter is 12 mm.

*Bud form.*—Urceolate.

*Sepal inner surface.*—Color: Yellow-Green Group 146D. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—About 35 mm long, 6 mm wide.

*Receptacle.*—Texture: Smooth. Size: 5 mm in height, 6 mm wide. Color: Yellow-Green Group 144A. Shape: Funnel.

*Pedicel.*—Surface: Smooth. Length: About 70 mm. Diameter: 3 mm on average. Color: Yellow-Green Group 144A. Strength: Strong.

*Peduncle.*—Length: 1 mm. Diameter: About 3 mm. Color: Yellow-Green Group 145A. Texture: Smooth.

Flower bud development: Flower buds are borne single or in clusters of about 3 flower buds per stem.

Flower bloom:

*Fragrance.*—Moderate to light floral scent.

*Duration.*—The blooms have a duration on the plant of approximately 25 days. Petals fall cleanly away from plant after flowers have fully matured.

*Size.*—Flower diameter is 70 mm when open. Flower depth is 23 mm.

*Flower shape.*—Rosette with many slightly overlapping petals of different sizes.

*Shape of flower, side view.*—The upper portion is convex. The lower portion is flat.

Petalage: Under normal conditions, flowers have about 38 petals.

General tonality of flower: Open flowers are Yellow Group 6A.

Petal color:

*Upon opening, outer and inner petals.*—Upper surface: Yellow Group 6A Lower surface: Yellow Group 6A. Guard petals have intonations of Yellow-Green Group 143C.

*Basal petal spots.*—No distinctive coloration at the petal base observed.

*After opening, outer petals.*—Upper surface: Yellow Group 6A. Lower surface: Yellow Group 6A.

*After opening, inner petals.*—Upper surface: Yellow Group 6A. Lower surface: Yellow Group 6A.

*Basal petal spots, after opening.*—No distinctive coloration at the petal base observed.

Petals:

*Petal reflex.*—Moderate to strong, bilateral.

*Margin.*—Entire and uniform. Moderate undulations.

*Shape.*—Broad and elliptic. Apex shape: Rounded. Base shape: Broad.

*Size.*—31 mm (l)×31 mm (w).

*Texture.*—Smooth.

*Thickness.*—Thick.

Petaloids:

*Size.*—16 mm (l) by 11 mm (w).

*Quantity.*—About 5.

*Shape.*—Mostly round with irregular margins.

*Color.*—Yellow Group 6A on the upper and lower side.

Reproductive flower parts:

*Pollen.*—None observed.

*Anthers.*—Size: 2 mm in length. Color: Greyed-Orange Group N163D. Quantity: 55 on average.

*Filaments.*—Color: Yellow Group 13B. Length: 6 mm.

*Pistils.*—Length: 6 mm. Quantity: 30 on average.

*Stigmas.*—Color: Greyed-Yellow Group 162D.

*Styles.*—Color: Red Group 42C.

*Location of stigmas.*—Level in location relative to the length of the filaments and the height of the anthers.

*Hips.*—None Observed.

PLANT

Plant growth: Upright. Plants are 55 cm in height, and 33 cm wide.

Stems:

*Color of juvenile growth.*—Yellow-Green Group 144B.

*Color of mature growth.*—Yellow-Green Group 144A.

*Length.*—Canes are about 20 to 30 cm from the base of the plant to the flowering portion.

*Diameter.*—4 to 5 mm.

*Internodes.*—On mature canes about 35 mm between nodes.

*Surface texture.*—Young wood: Smooth. Older wood: Smooth.

Long prickles:

*Incidence.*—About 10 prickles per 10 cm of stem.

*Size.*—Average length of prickles on mature stems is 6 mm.

*Shape.*—Upper portion is linear. Lower portion is concave.

*Color.*—Juvenile prickles: Greyed-Purple Group 184A. Mature prickles: Greyed-Purple Group 184A.

Plant foliage:

*Compound leaf.*—130 mm (l)×85 (w).

*Quantity.*—2 or 3 leaves per 10 cm of stem on average.

*Leaf bearing angle to the stem.*—90 degrees.

*Color of juvenile foliage.*—Upper side: Yellow-Green Group 144A with intonations of Greyed-Orange Group 175A at margins. Lower side: Yellow-Green Group 144B.

*Color of mature foliage.*—Upper side: Yellow-Green Group 147A. Lower side: Yellow-Green Group 147B.

Plant leaves and leaflets:

*Stipules.*—Size: 17 mm long, mm wide. Quantity: 2 per compound leaf. Shape: Linear, slightly broad based with outward extending apices. Margins: Finely serrated. Color: Yellow-Green Group 144A.

*Petiole.*—Length: About 18 mm. Diameter: 2 mm. Upper surface color: Yellow-Green Group 144A. Lower surface color: Yellow-Green Group 144A.

*Rachis*.—Length: About 52 mm. Upper surface color: Yellow-Green Group 144A. Lower surface color: Yellow-Green Group 144A.

*Leaflet*.—Quantity: Normally 7 leaflets. Margins: Serrated. Size: Terminal leaflets are about 56 mm long, 37 mm wide. Shape: Generally elliptical. Base: Rounded. Apex: Acuminate. Texture: Smooth. Thickness: Average. Arrangement: Odd pinnate. Venation: Reticulate. Glossiness: Glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulpah112' substantially as described and illustrated herein.

* * * * *

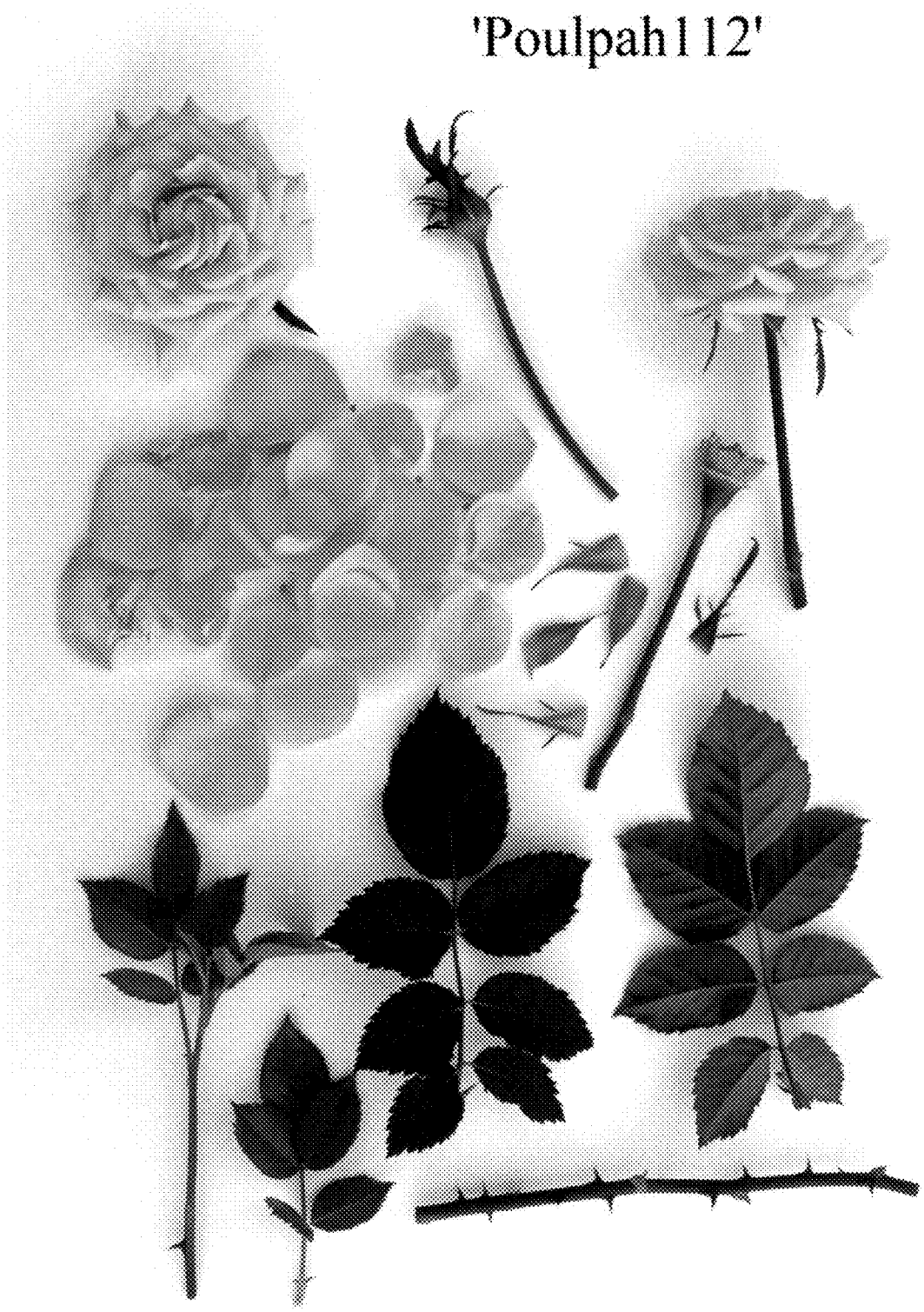

'Poulpah112'